(12) United States Patent
Lebner

(10) Patent No.: US 7,838,718 B2
(45) Date of Patent: *Nov. 23, 2010

(54) DEVICE FOR LACERATION OR INCISION CLOSURE

(75) Inventor: Michael Lebner, Wellesley Hills, MA (US)

(73) Assignee: Clozex Medical, LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/626,040

(22) Filed: Jul. 24, 2003

(65) Prior Publication Data

US 2005/0020957 A1  Jan. 27, 2005

(51) Int. Cl.
*A61F 13/00* (2006.01)
(52) U.S. Cl. .................... 602/54; 602/41; 602/52; 606/213; 606/214; 606/215
(58) Field of Classification Search ............ 602/41–59; 606/213–516; 128/888, 889
See application file for complete search history.

(56) References Cited

U.S. PATENT DOCUMENTS

| | | |
|---|---|---|
| 1,074,413 A | 9/1913 | De Baun et al. |
| 1,230,444 A | 6/1917 | Teed |
| 1,969,188 A | 10/1932 | Spicer |
| 2,196,296 A | 4/1940 | Flynn |
| 2,532,011 A | 11/1950 | Dahlquist et al. |
| 2,818,865 A | 9/1953 | Jacoby, Jr. |
| 2,762,371 A | 9/1956 | Guio |
| RE24,906 E | 12/1960 | Ulrich |
| 3,020,186 A | 2/1962 | Lawrence |
| 3,329,548 A | 7/1967 | Blatz |
| 3,389,827 A | 6/1968 | Abere |
| 3,645,835 A | 2/1972 | Hodgson |
| 4,112,213 A | 9/1978 | Waldman |
| 4,141,363 A | 2/1979 | James et al. |
| 4,310,509 A | 1/1982 | Berglund et al. |
| 4,323,557 A | 4/1982 | Rosso et al. |
| 4,328,057 A | 5/1982 | Gutow |
| 4,374,520 A | 2/1983 | Grossmann |
| 4,413,621 A | 11/1983 | McCracken |
| 4,423,731 A | 1/1984 | Roomi |
| 4,472,480 A | 9/1984 | Olson |
| 4,485,809 A | 12/1984 | Dellas |
| 4,499,896 A | 2/1985 | Heinecke |
| RE31,887 E | 5/1985 | Hodgson |
| 4,524,095 A | 6/1985 | Gockel et al. |
| 4,545,371 A | 10/1985 | Grossmann |
| 4,549,063 A | 10/1985 | Ang |
| 4,587,146 A | 5/1986 | Anhauser |
| 4,590,022 A | 5/1986 | Cioca |
| 4,595,001 A | 6/1986 | Potter |
| 4,595,011 A | 6/1986 | Phillips |
| 4,596,738 A | 6/1986 | Metcalfe |
| 4,600,001 A | 7/1986 | Gilman |
| 4,614,183 A | 9/1986 | McCracken |
| 4,646,731 A | 3/1987 | Brower |
| 4,664,106 A | 5/1987 | Snedeker |
| 4,678,462 A | 7/1987 | Vaillancourt |
| 4,706,662 A | 11/1987 | Thompson |
| 4,737,410 A | 4/1988 | Kantner |
| 4,753,232 A | 6/1988 | Ward |
| 4,787,380 A | 11/1988 | Scott |
| 4,825,866 A | 5/1989 | Pierce |
| 4,926,850 A | 5/1990 | Lott et al. |
| 4,950,282 A | 8/1990 | Beisang |
| RE33,353 E | 9/1990 | Heinecke |
| RE33,727 E | 10/1991 | Sims |
| 5,088,483 A | 2/1992 | Heinecke |
| 5,106,383 A | 4/1992 | Mulder |

(Continued)

FOREIGN PATENT DOCUMENTS

GB          1299367          12/1972

(Continued)

OTHER PUBLICATIONS

Packaging and instruction sheet for "umbillical hernia plaster" produced by Lohmann GmbH & Co., KG (Postfach 23 43, D-56513 Neuwied, Germany); undated.

(Continued)

*Primary Examiner*—Kim M Lewis
(74) *Attorney, Agent, or Firm*—Kevin M. Farrell; Katherine A. Wrobel; Pierce Atwood LLP

(57) ABSTRACT

The disclosed two-component device includes a first component comprising a first adhesive-backed anchoring member and one or more first connecting members, produced separately from the first adhesive-backed anchoring member. The first connecting member is attached to the first adhesive-backed anchoring member, extending from One edge thereof in a first direction. Also disclosed is a second component comprising a second adhesive-backed anchoring member and one or more second connecting members, produced separately from the second adhesive-backed anchoring member. The second component is attached to the second adhesive-backed anchoring member, extending from one edge thereof in a second direction generally opposite to the first direction. Adhesive for attaching the one or more first connecting members to the second anchoring member and adhesive for attaching the one or more second connecting members to the first anchoring member is provided. Methods of use are also disclosed.

34 Claims, 3 Drawing Sheets

U.S. PATENT DOCUMENTS

| | | | |
|---|---|---|---|
| 5,135,518 A | 8/1992 | Vera | |
| 5,160,315 A | 11/1992 | Heinecke | |
| 5,176,703 A * | 1/1993 | Peterson | 606/216 |
| 5,263,970 A | 11/1993 | Preller | |
| 5,336,162 A | 8/1994 | Ota | |
| 5,425,702 A | 6/1995 | Carn et al. | |
| 5,531,855 A | 7/1996 | Heinecke et al. | |
| 5,534,010 A | 7/1996 | Peterson | |
| 5,685,833 A | 11/1997 | Turngren | |
| 5,733,251 A | 3/1998 | Johns | |
| 5,733,570 A | 3/1998 | Chen | |
| 5,738,642 A | 4/1998 | Heinecke et al. | |
| 5,779,659 A | 7/1998 | Allen | |
| 5,849,325 A | 12/1998 | Heinecke | |
| 5,891,078 A | 4/1999 | Turngren | |
| 5,979,450 A | 11/1999 | Baker et al. | |
| 5,981,823 A | 11/1999 | Turngren | |
| 6,129,971 A | 10/2000 | Brandt | |
| 6,149,614 A | 11/2000 | Dunshee | |
| 6,169,224 B1 | 1/2001 | Heinecke | |
| 6,264,976 B1 | 7/2001 | Heinecke | |
| 6,329,564 B1 * | 12/2001 | Lebner | 602/41 |
| 6,364,188 B1 | 4/2002 | Dunshee | |
| 6,420,622 B1 | 7/2002 | Johnston | |
| 6,436,432 B2 | 8/2002 | Heinecke | |
| 6,461,467 B2 | 10/2002 | Blatchford | |
| 6,495,230 B1 | 12/2002 | do Canto | |
| 6,548,727 B1 | 4/2003 | Swenson | |
| 6,566,575 B1 | 5/2003 | Stickels | |
| 6,596,917 B2 | 7/2003 | Oyaski | |
| 6,607,799 B1 | 8/2003 | Heinecke | |
| 6,822,133 B2 * | 11/2004 | Lebner | 602/54 |
| 6,831,205 B2 * | 12/2004 | Lebner | 602/42 |
| 6,982,359 B1 * | 1/2006 | Beaudry | 602/54 |
| 2004/0106888 A1 * | 6/2004 | Lutri et al. | 602/54 |
| 2004/0193216 A1 * | 9/2004 | Deutsch | 606/216 |
| 2004/0204740 A1 | 10/2004 | Weiser | |
| 2004/0243040 A1 | 12/2004 | Weiser | |
| 2005/0182443 A1 | 8/2005 | John | |

FOREIGN PATENT DOCUMENTS

WO    WO2005/079674 A1    1/2005

OTHER PUBLICATIONS

Stalar: "A more effective way to wound closure," by S. Paris, Abstract, Pub. by 43 Intern'l Sci. and Eng. Fair, Nashville, Tennessee, May 10, 1992, p. 257.

Paris, Stacy: "Is there a more effective way to accomplish wound closure than those presently employed?"; author indicates abstract published by South Carolina Junior Academy of Science, Feb. 1991; applicants have not independently verified this publication date.

* cited by examiner

DEVICE FOR LACERATION OR INCISION CLOSURE

BACKGROUND OF THE INVENTION

Devices and methods for laceration or incision closure are known in the art. The use of sutures, staples or clamps to close a laceration or incision represents the most common of these prior art techniques. The use of sutures, staples or clamps is an invasive technique that can be painful and requires the use of an anesthetic. These processes often leave unsightly scars, both from the insertion holes and from varying tensions applied to the laceration or surgical incision between suturing points and intervening spaces. Moreover, these methods necessitate follow-up visits to a hospital or doctor's office for removal.

Although other devices and methods for closing lacerations or incisions are known in the art, these have not gained popular acceptance due to limitations in their design. There is a clear need for non-, or less invasive methods for laceration or incision closure which is practical and easy to use.

SUMMARY OF THE INVENTION

The present invention relates to a two-component device useful for closing a laceration or incision. The first component of the device includes an adhesive-backed anchoring member, and one or more first connecting members extending from a first edge of the anchoring member. The first edge of the anchoring member is also referred to herein as a wound edge because, in use, the first edge is placed along one edge of the laceration or incision. The connecting members are, generally speaking, elongated and strap-like in configuration. That is, the width of the connecting members is substantially greater than their thickness. The second component of the device also includes an adhesive-backed anchoring member, and one or more connecting members extending from a first edge of the anchoring member of the second component of the device. As was the case with the first component of the device, the first edge of the anchoring member of the second component is also referred to herein as a wound edge.

The first and second components of the device are generally produced from sheets or rolls of a polymeric material, or a polymeric composite. The sheet or roll stock is typically referred to as "film" as the thickness of the stock in preferred embodiments ranges from about 0.5 mil to about 5 mil. As is discussed in greater detail below, the first and second components may be produced individually as monolithic components (having no joints or seams). Such monolithic components are produced from single stock material. This stock must be substantially inelastic, as any stretching which could allow the laceration or incision to open is clearly undesirable. Alternatively, polymeric materials which are elastic may be used if they are reinforced with an inelastic structural material. Such reinforced polymers are referred to herein as polymeric composites. A reinforcing, inelastic structural material is referred to in the art as "scrim." Scrim may be a woven textile or polymer, a non-woven polymer or any other structural entity that acts to stabilize the substrate. Preferably, the scrim reinforced substrate will have a high degree of air permeability (e.g., 1,000 to 8,000 liters/sec/m$^2$).

Additionally, non-reinforced polymers exhibiting a degree of elasticity may be used in the production of anchoring members for embodiments in which anchoring members and connecting elements are produced separately, and subsequently attached. If a non-reinforced elastic polymer is used to produce an anchoring member, it will be preferable to reinforce the upper surface of the wound edge with an inelastic element so that wound edge remains substantially straight across the incision site during the closure process. Such an element is referred to herein as a "wound edge bar." Vapor permeable polymeric materials that satisfy the other requirements for use in the manufacture of the device offer improved comfort and are preferred. Transparent stock is also preferred so that the healing process of the entire wound site can be monitored easily.

The first and second components are cut from sheet stock by any conventional process. Die cutting from sheet or roll stock is one method that may be employed. Laser and ultrasonic trimming devices are also examples of equipment that may be used to cut the components of the present invention.

The specification of a particular device such as the size of the anchoring members, and length and width of connecting members, is dictated primarily by functional considerations. For example, a surgical procedure such as a Cesarean-section is a procedure for which a high degree of security in closure would be of primary concern. The abdomen provides a large surface for adhesive attachment, and anchoring members and connecting members would be over-sized to provide a high degree of security. The practical limits to over-sizing the components are dictated only by skin surface available for effective attachment. Thus, for a Cesarean-section, an anchoring member extending from the point of incision, around to the back of the individual could be used. For small lacerations in visible locations, such as the face, very small anchoring members (e.g., ¼ inch by ½ inch) may be appropriate. Although it is convenient for manufacturing purposes, there is no requirement for symmetry in the device of the present invention. That is, the anchoring member of the first component need not be identically shaped to that of the second component. Furthermore, it is not a requirement of the device that the first and second components have the same number of connecting members or be produced from the same sheet stock.

Devices of the present invention are easily cut and trimmed for secure application. For example, the anchoring member of one component may be trimmed to avoid application to an area where such application would inevitably result in a lifted-adhesive edge which could result in premature release of the entire device.

A number of embodiments of the device are disclosed herein. Features of particular importance include: the use of transparent stock for the production of the first and second components; the selective application of adhesive to portions of the lower surfaces of connecting members; connecting members having less average width in the bridging portion relative to the attached portion; the use of a two-stage release liner system; and the separate production of connecting members and anchoring members followed by attachment to form individual first and second components. A device of the present invention may contain one or more of the disclosed features, in any combination thereof. These features will be discussed in greater detail below.

The adhesives selected for use in connection with the present invention must meet a number of requirements. First, adhesive which is to come into contact with the skin must be selected to minimize the potential for adverse reaction by the skin. That is, the adhesive selected should be hypoallergenic. Additionally, all adhesives, whether or not they are intended to contact the skin, must provide a secure hold for a period of time sufficient for the healing process to progress to the point where removal of the device is appropriate. An adhesive hold period of about 7-10 days is generally suitable.

The use of the device to close a laceration or incision will be discussed in greater detail below, however, a brief orientation at this stage in the discussion is helpful. In use, the adhesive-backed anchoring member of the first component of the device is applied to the skin of the animal or human patient adjacent to the laceration or incision to be closed. The device of the present invention is produced in a variety of sizes, or may be used in series, to close lacerations or incisions of varying lengths. The wound edge of the first component is placed very near to the edge of the laceration or incision, but not so close as to introduce adhesive from the first component anchoring member into the open area of the laceration or incision. The one or more connecting members extend from the wound edge of the anchoring member of the first component, in a direction which is generally perpendicular to the wound edge, and extend across the area of a laceration or incision to the opposite side of the laceration.

A similar application procedure is followed for application of the second component, the procedure for the application of the second being the mirror image of the procedure for application of the first. Following application of the anchoring members, the laceration is closed by either pushing anchoring members toward one another, or by pulling them together by grasping one or more connecting members from each component and pulling the laceration closed. Very fine adjustment can be made in the X and Y dimension ensuring laceration closure with minimal scarring. When the first and second component are positioned to the satisfaction of the physician, or other individual applying the device, the relationship of the two components is fixed by attaching the one or more connecting members of the first component to the anchoring member of the second component, and by attaching the one or more second connecting members of the second device to the anchoring member of the first device.

Adhesive is a preferred means of attaching one or more connecting members to an anchoring member. In one embodiment, adhesive is applied to at least a portion of the lower surface of the connecting members for attaching the connecting members of one of the two components to the applied anchoring member of the other component. The connecting members have two parts or portions—an attached portion and a bridging portion. The attached portion of the connecting members, as the name indicates, is that portion which is attached to the anchoring member of the opposing component following application of the device. The bridging portion is the portion of the connecting member or members which spans the over-laceration area. In further refined embodiments, the lower surface of the bridging portion contains less adhesive than the attached portion. In preferred embodiments, the entire bridging portion of the one or more connecting members are free of adhesive or alternately have adhesive, but this is blocked with another film (kill layer) to render the adhesive in the bridging portion nonfunctional.

As mentioned above, the dimension of the connecting members is strap-like in that their width is substantially greater than their thickness. In light of the fact that the point of attachment between the first and second components is between the underside of attached portions of connecting members with the upper surface of attached anchoring members, maximizing the area of contact will result in a more secure closure of the device because the area of adhesive contact is maximized. Thus, from the standpoint of security of closure, wider connecting members are preferred. However, as the width of all the connecting members is increased, the distance between connecting members necessarily is decreased. It is extremely important that there be enough distance between adjacent connecting members to facilitate fine adjustment of the device as the second anchoring member is being positioned, and after the two anchoring members are positioned, but prior to fixing their relationship by attaching connecting members to anchoring members.

As was stated in U.S. Pat. No. 6,329,564, the disclosure of which is incorporated herein by reference:

> There is no absolute minimum which can be stated with respect to spacing between elongated connectors [connecting members]. Preferred ranges are probably best stated as a percentage of device length (i.e., the dimension of the device generally parallel the laceration or incision). For example, a spacing of between about 5% to about 10% of the bandage length is an example of an appropriate range.

This spacing provides substantial adhesive contact between attached portions of connecting members with anchoring members, as well as sufficient spacing for fine adjustment of both before and following the attachment of the second anchoring member. Fine adjustment made after the attachment of the second anchoring member is generally a concern after the laceration has been closed and just prior to attachment of connecting members to anchoring members. At this stage in the application process, the bridging portions of the one or more first connecting members and the bridging portions of the one or more second connecting members are aligned with one another over the closed laceration or incision. In a preferred embodiment of the present invention, the average width of the bridging portions is less than the average width of the attached portions of the connecting members. Average width is determined by measuring from the outer perimeters of the bridging portions and the outer perimeters of the attached portions.

This difference in width in the bridging portion relative to the attached portion affords advantages over prior art devices in which the width of connecting members was substantially constant along their length. Consider, for example, a prior art device designed for maximum security. In such a device, the connecting members would be placed as close as possible, while still providing for a minimum acceptable degree of adjustment range. If the bridging area were narrowed in such a device, the net effect would be an increase in exposed area over the laceration (which is desirable for application of medicines, removal of exudates, etc), as well as an increase in the range of adjustment (narrowing the width of the connecting members in the bridging portion effectively increases the distance between adjacent bridging portions).

Considering the same prior art device discussed in the preceding paragraph, holding the width of bridging portion constant, while increasing the width of the attached portions provides for greater security as the area of adhesive contact is effectively increased. It will be recognized by one skilled in the art that hybrid configurations (i.e., devices having narrowed bridging portions and widened attached portions relative to prior art, uniform width devices) represent important embodiments of the present invention.

Preferred embodiments of the present invention include pulling elements which are attached to connecting members, or to extensions of connecting members. Extensions of connecting members could themselves be considered to be pulling elements in embodiments in which only one connecting member is associated with a component. By definition, the attached portion of a connecting member attaches to the anchoring member of another component. Extensions of a connecting member extend the length of the connecting member for ease of application, and are generally removed following the application process. Perforations are preferably provided to facilitate their removal. For embodiments in which the number of connecting members associated with a component is greater than one, a pulling element is useful for joining the connecting members or extensions of connecting members to enable a user to easily apply a pulling force to more than one connecting member.

To minimize confusion for new users of the device of the present invention, the pulling elements and anchoring members may be coded to enable user distinction. Thus, for example, the coding may comprise an observable geometric distinction between the shape of the pulling elements and the shape of the anchoring members. In another embodiment, such coding may comprise printed indicia to enable user distinction between the components. Colors may also be used to provide this distinguishing function.

The device of the present invention includes a minimum of one connecting member associated with each component of the two-component device. For embodiments in which each component includes two or more connecting members, and the connecting members are attached to pulling elements, the issue of interlacing the connecting members of the two components presents itself. This issue was discussed in U.S. Pat. No. 6,329,564, the disclosure of which is incorporated herein by reference. Briefly, in order to assemble an interlaced device it may be necessary to construct the first component and the second component independently, and subsequently cut one of the two components in order to interleave connecting members. The cut can be rejoined using an adhesive backed film or tape. Alternatively, at least one of the two components can be incompletely produced enabling interlacing, followed by completion of the device (e.g., by the addition of a pulling element).

The adhesive-backed surfaces of the device of the present invention are protected (e.g., from contamination and oxidation) by the application of release liners during the manufacturing process. In some instances, multiple release liners, or release liner systems may be used to protect a single, uninterrupted, adhesive-backed surface. Consider, for example, the anchoring members of the disclosed device. In order to precisely attach the wound edge of an anchoring member adjacent a laceration or incision to be closed, it is preferable to hold the anchoring member with one hand leaving the other hand free to manipulate the laceration or incision area. Thus, a plurality of release liners on each anchoring member is preferred. A first release liner, which protects the wound edge, is removed first during the application process. In this way, a portion of the wound edge can be adhered to the skin while leaving a protected portion of the anchoring member which can be held (e.g., in a gloved hand) without the device adhering to the fingers of the user. Once the wound edge has been applied, the second release liner can be removed to fully secure the anchoring member. The use of a plurality of release liners in connection with the adhesive associated with the connecting members is less important as extensions of the connecting members and pulling elements are provided "adhesive-free" in preferred embodiments. To minimize confusion for new users of the device of the present invention, the release liners may be also be coded. Release liner colors or printed indicia on the release liner are examples of coding enabling a user to readily identify the order of release liner removal.

As discussed above, the film or sheet stock used to manufacture the first and second components of the device of the present invention can be, and preferably are, extremely thin. When applying an anchoring member produced from such thin stock next to a laceration or incision, it is easy to imagine difficulties associated with wrinkling and overlapping of edges, inadvertent or incorrectly positioned initial contact, etc. The release liners employed in connection with the device can provide substantial aid in working with the device, particularly a device produced from thin sheet stock, if properly selected. For example, if two release liners are used to protect the adhesive-backed surface of an anchoring member, the characteristics of the release liner protecting the wound edge of the anchoring member is far less important than the characteristics of the later-removed, second release liner protecting the anchoring member. If, for example, a semi-rigid second release liner is employed, this will enable more precise placement of the wound edge of the anchoring member.

In developing the device of the present invention, the placement of the initial components is most important in achieving the best cosmetic results. A positioning technique which has proven to be effective requires the use of alignment indicators on the anchoring members for precisely placing them and an application technique referred to as "Straightening the Wound Edge" that uses a semi-rigid release liner (or release liner system, as discussed below) to apply each anchoring member following the exposure of adhesive at the wound edge.

As most incisions tend to be almond shaped, the technique is referred to as "Straightening the Wound Edge." This technique is used as there are few lacerations having edges that are perfectly straight and the device works best when the edges of a laceration or incision are substantially straightened. It has also been demonstrated clinically that all shaped wounds can be segmented into smaller parts that can be closed straight and this provides applicability of the invention by using the devices in sequence to all shaped wounds.

Optionally, on each anchoring member, at the midpoint of the wound edge, there is an arrow (or other mark or indicia) referred to as an "alignment indicator" that is used in the placement procedure of the device. Such alignment indicators are helpful in positioning the anchoring members.

More specifically, an application procedure is outlined as follows:

1. Prior to application of the device, the clinician manually closes the edges of the laceration or incision and places a dot with a surgical pencil on both sides of the laceration or incision at the center (the "alignment marks") about $\frac{1}{16}$" back from the edge of the laceration or incision. The device can then be applied.
2. Following exposure of the adhesive at the wound edge (e.g., by removing a first release liner), the anchoring member is held between the thumb and middle finger of one hand. The semi-rigid release liner (or release liner system) is then bent by pinching the ends together using the thumb and middle finger forcing the release liner, and the attached anchoring member, including the wound edge, to adopt a U-shaped conformation. The forefinger can assist by pushing the midpoint of the wound edge to the bottom of the U-shaped position. The central portion of the wound edge (i.e., the portion at the bottom of the U-shaped conformation) at the alignment indicator is then the first point of contact as the device is applied to the alignment mark about $\frac{1}{16}$" back from the wound edge. The device is then manipulated to straighten the laceration or incision edge, and the remaining portion of the wound edge is then slowly lowered into contact with the skin. This step is followed by removal of the remaining release liner(s) thereby completing the attachment, securing the remainder of the anchoring member, and achieving a substantially straight wound edge.

Development of the release liner systems has resulted in a further improved embodiment which is described herein as a two-stage release liner system referred to as the "flip tab". This system provides a number of advantages which will be discussed in detail. The two-stage release liner system includes a single release liner with a bottom surface covering the entire adhesive-backed surface of an anchoring member. Attached to the exposed surface of the wound edge portion of the release liner protecting the wound edge is a semi-rigid tab having a first and a second edge. The first edge is substantially linear and oriented generally parallel to the wound edge of the anchoring member and attached to the release liner at a position intermediate in the release liner between the portion of the release liner protecting the wound edge and the portion of the release liner protecting the edge of the anchoring member generally opposite the wound edge. The second edge of the tab extends unattached beyond the wound edge. To attach an anchoring member protected by the flip tab two-stage release liner system, a user simply contacts the portion of the semi-rigid tab extending beyond the wound edge (e.g., with a thumb), and while holding the component (e.g., by the connecting members attached to the anchoring member to be applied), flips back or folds the semi-rigid tab (and attached release liner) over onto the portion of the release liner which is not attached to the semi-rigid tab. This provides for exposure of the adhesive at the wound edge, as well as for the handling advantages discussed above which are provided by the association of the semi-rigid tab with the anchoring member during the placement of the wound edge. When the placement of the wound edge is complete, the semi-rigid tab is grasped between the thumb and forefinger and pulled, thereby removing the entire release liner.

With respect to the flip tab two-stage release liner system, it is important that when the semi-rigid tab is flipped-back onto the portion of release liner to which it is not attached by adhesive, that the portion of the release liner to which the tab is not attached remains fully adhered to the anchoring member. During the development process, it was discovered that many of the release liners employed did not fold over cleanly as the tab was flipped back. When using release liners exhibiting this characteristic, it is desirable to crease the release liner in the area of the release liner which is not attached to the tab, immediately adjacent the tab, to create a hinge region. Release liners that did not perform in the desired manner proved to work exceptionally well following the application of the crease. The crease can be applied in any number of ways which will be apparent to one skilled the art. When working on a small scale in the development process it was sufficient to run a dull knife down the release liner using the attached semi-rigid tab as a guide.

It will be recognized that the two-stage release liner system disclosed herein finds application in connection with products other than the disclosed laceration closure device. The system can be employed in connection with any adhesive-backed surface which is protected by a release liner. In the most general form, the two-stage release liner system includes a release liner with a bottom surface covering the adhesive-backed surface of an article. A tab is attached to a portion of the top surface of the release liner, the tab comprising a first and a second edge. The first edge of the tab is substantially linear and attached to a portion of the release liner, the second edge extends beyond the boundary of the adhesive-backed surface.

The embodiments of the device discussed above comprise first and second components which are monolithic in nature. That is, the first component (which includes an anchoring member and one or more connecting members) is produced from a single sheet of stock material without joints or seams. The same statement applies to the second component. In an alternative embodiment, the first and second components are not monolithic in nature. This alternative embodiment is based on the recognition that the desired physical properties of the anchoring members and the connecting members are not, in every instance, identical. For example, a degree of elasticity is a desirable feature in an anchoring member when applied, for example, to an area such as a joint. An anchoring member produced from a film having a degree of elasticity is less likely to release prematurely than an anchoring member produced from a substantially inelastic material when applied to such an area. Elasticity is a property to be avoided when producing connecting members. Any stretching of connecting members is to be avoided as this will tend to allow premature opening of a laceration or incision.

In embodiments in which the first and second components are not monolithic, anchoring members may be produced from stock having a degree of elasticity. Connecting members are produced separately from stock which is substantially inelastic. One ore more first connecting members are then attached (e.g., with adhesive) to a first anchoring member to produce a first component. A second component is similarly constructed.

It is not a requirement that connecting members and anchoring members of non-monolithic components be produced from different stock material. It may be desirable, for example, to create an overlap in a portion of the connecting members (e.g., the bridging portion) in order to provide for additional strength. Thus, double-thickness in the bridging area may be provided by producing a monolithic anchoring member including a portion of connecting member. A separately produced connecting member is then attached, in an overlapping manner, to the monolithic anchoring member. This creates a first component which is double-thick in the bridging portion for additional strength and further eliminates stretching.

It may be desirable to reinforce the wound edge portion of the anchoring member with another layer of less flexible stock. This "wound edge bar" would provide better translation of the force applied by the connecting members uniformly along the entire wound edge. Similarly, it may be desirable to reinforce the optional pulling element, or a portion thereof, with another layer of less flexible stock. This "pull bar" would be useful in applying uniform tension from the pulling element to all connecting members, as the device is positioned for closure. This feature would become more important in embodiments of the device intended to close long lacerations or incisions where there might be up to four or more connecting members to be pulled and secured to each anchoring member.

The present invention also relates to methods for closing a laceration or incision using a device of the type described above. Such methods include the steps of applying the anchoring member of a first and second component on opposing sides of a laceration or incision to be closed. The laceration is then closed by the user either by pushing the edges of the laceration together by manipulating the skin in the area of the anchoring members, by pulling the laceration closed using connecting members (or extensions of connecting members, or pulling elements, if present), or by some combination thereof. Once the laceration is closed, the position of the first and second component relative to each other is fixed by attaching the connecting members to the anchoring members.

DETAILED DESCRIPTION OF PREFERRED EMBODIMENTS

Figure 1:
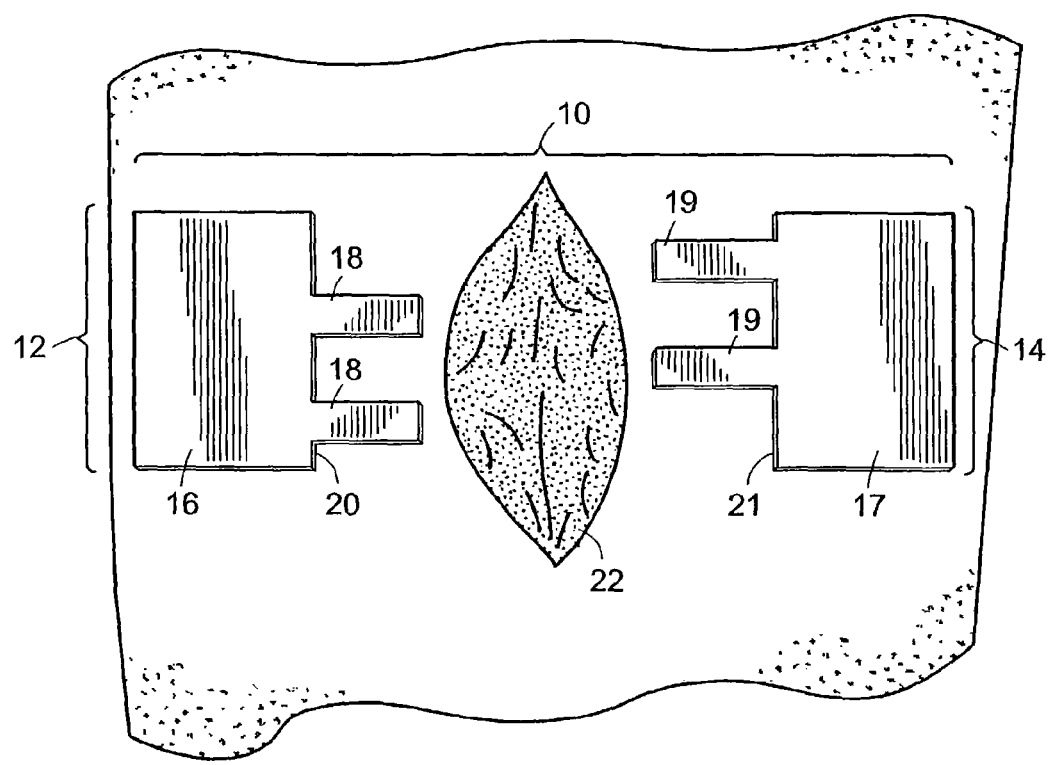
FIG. 1 is a top view illustrating the two components of a device of the present invention in a non-applied state.

The two components (12 and 14) of a two-component device of the present invention (10) are shown in FIG. 1. First component (12) includes an anchoring member (16) and a plurality of connecting members (18) extending from a first edge of the device (20) which is also referred to herein as the wound edge. Similarly, the second component (14) includes an anchoring member (17) and a plurality of connecting members (19) extending from a first edge (21) of the device which is also referred to as a wound edge. Anchoring members (16 and 17) have a lower surface (not shown in FIG. 1) which is coated with an adhesive suitable for attachment of the components to the skin. In preferred embodiments, a portion of the lower surface (not shown in FIG. 1) of connecting members (18 and 19) are coated with an adhesive for attachment of the connecting members of one component to the anchoring member of the second component. An incision (22) is also shown in an open state.

Figure 2:
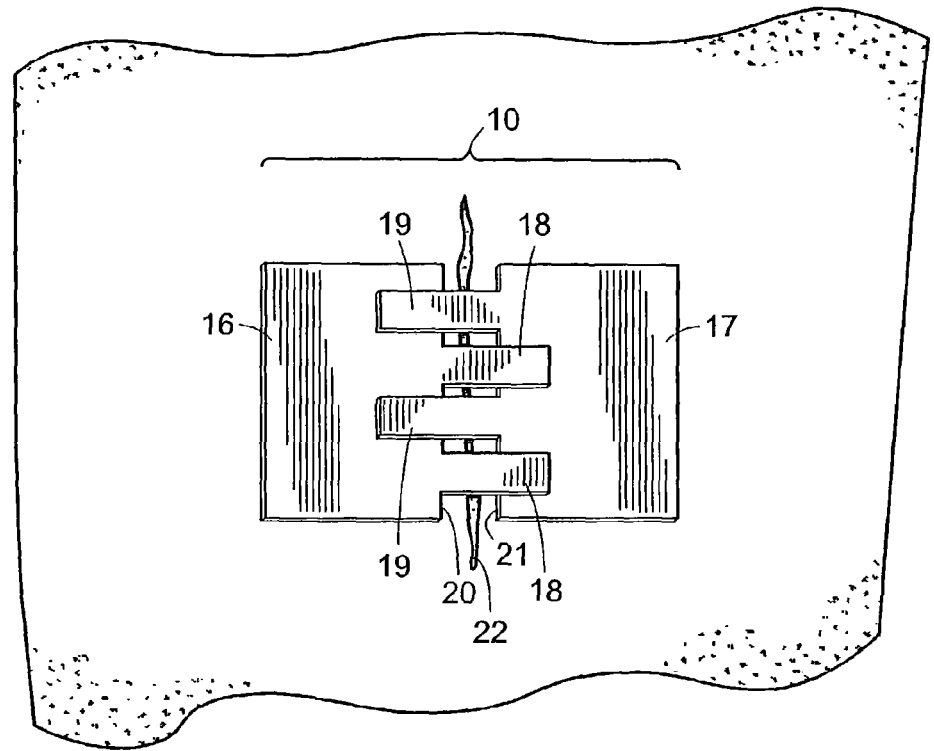
FIG. 2 is a top view illustrating the two components of a device following application.

Referring to FIG. 2, the device of the present invention (10) is shown in the applied state with the two anchoring members (16 and 17) being attached to the skin and connected to one another by connecting members (18 and 19). A closed incision (22) is also shown in FIG. 2. The portion of the connecting members (18 and 19) spanning the over-laceration area between the anchoring members (16 and 17) is referred to as the bridging portion, and the portion of the connecting members (18 and 19) which is attached to the anchoring member of another component is referred to as the attached portion. Wound edges of the device 20 and 21 are also shown in FIG. 2. The bridging portions and attached portions may be more clearly shown in FIG. 3 which follows.

Figure 3:
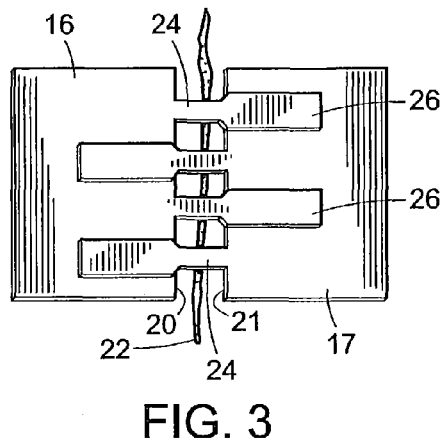
FIG. 3 is a top view illustrating an alternative embodiment of the device of the present invention, following application, in which the average width of the bridging portion of the connecting members is less than the average width of the attached portion of the connecting members.

Referring to FIG. 3, anchoring members (16 and 17) having wound edges (20 and 21) are shown in the attached state on opposing sides of an incision (22). Bridging portions (24) and attached portions (26) of connecting members are most readily seen is this drawing. In the embodiment depicted, the average width of the bridging portions (24) is less than the average width of the attached portions (26). In this embodiment, the average width of the attached portions (26) is substantially constant, whereas a narrowing cut is made to form the bridging portions (24). It should be noted that in the embodiment shown, a right angle cut defines the junction between the bridging portion (24) and anchoring member (16). In preferred embodiments, however, such right angle cuts are to be avoided as this can create points of weakness in the device. Thus, in preferred embodiments, the right angle cut at the junction between bridging element (24) and anchoring member (16) is replaced with a shouldered cut, such as the 45 degree cut shown at the junction between bridging portion (24) and attached portion (26).

Figure 4:
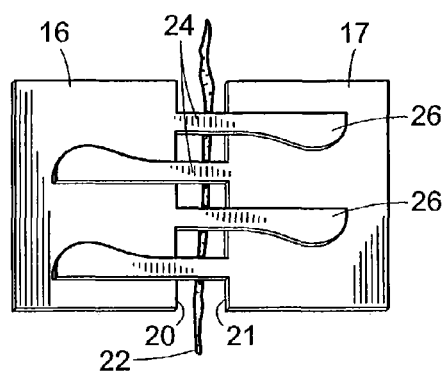
FIG. 4 is a top view illustrating an alternative embodiment of the device of the present invention, following application, in which the average width of the bridging portion of the connecting members is less than the average width of the attached portion of the connecting members.

Referring to FIG. 4, a second embodiment in which the average width of the bridging portions (24) is less than the average width of the attached portions (26) is shown. Also shown are anchoring members (16 and 17) having wound edges (20 and 21). Incision (22) is shown in the closed state. In the embodiment depicted in FIG. 4, the anchoring members (26) are flared to provide additional adhesive contact thereby providing for increased security of closure.

Figure 5:
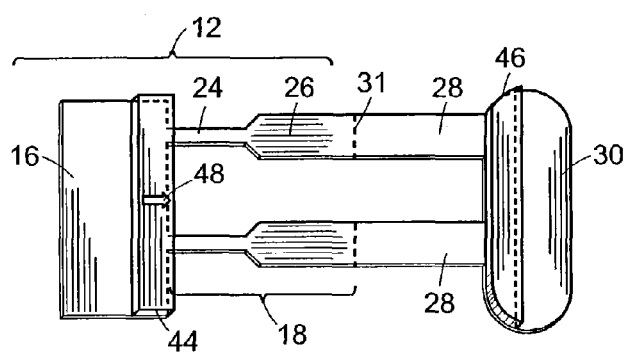
FIG. 5 is a top view illustrating one component of a two-component device of the present invention with optional pulling tab and connecting member extensions.

Referring to FIG. 5, a single component (12) of a two-component device of the present invention is depicted. The device includes an anchoring member (16) and a plurality of connecting members (18) having a bridging portion (24) and an attachment portion (26). Shown in FIG. 5 are optional extensions of connecting members (28), optional pulling element configuration (30), and optional perforations (31) for removal of extensions of connecting members (28) and pulling element (30). Also shown in FIG. 5 are optional wound edge bar (44), pull bar (46), and alignment indicator (48).

Figure 6:
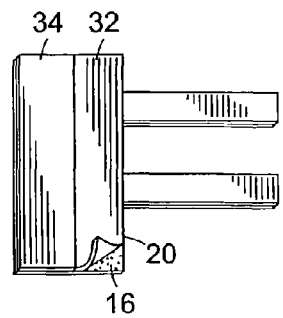
FIG. 6 is a bottom view of one component of a two-component device of the present invention illustrating an anchoring member protected by a plurality of release liners.

FIG. 6 is a bottom view of one component of a two-component device of the present invention illustrating an anchoring member (16) protected by a first release liner (32) and a second release liner (34). The first release liner (32) protects the adhesive at the wound edge (20) of the anchoring member (16). In use, the first release liner (32) is removed first and the wound edge (20) is applied to the skin. The presence of the second release liner (34) allows a user to hold the device while positioning the wound edge (20). In the preferred embodiment, there would be removal tabs to facilitate the removal of each liner that would be clear to one skilled in the art.

Figure 7A:
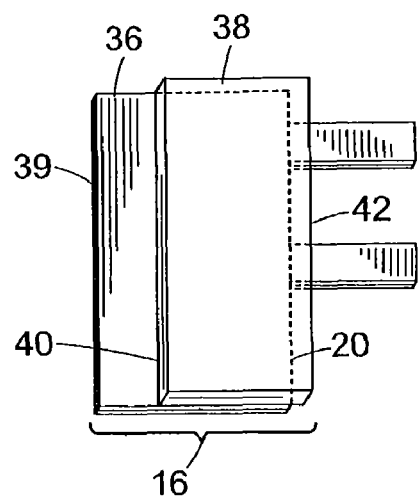
FIGS. 7A and 7B represent a bottom view of one component of a two-component device of the present invention illustrating a flip-tab two-stage release liner system in use.
Figure 7C:
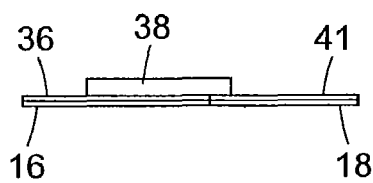
FIG. 7C illustrated an end view of this embodiment.
Figure 7B:
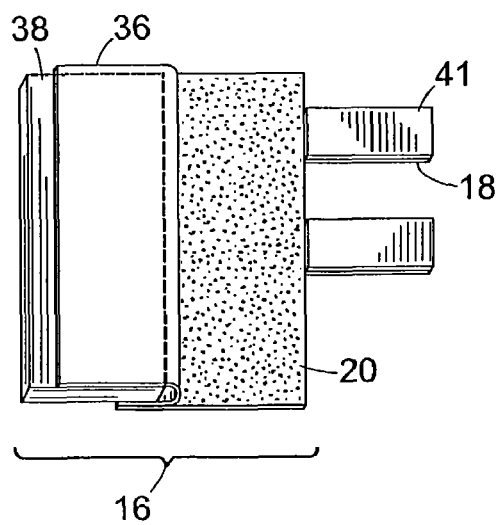

FIGS. 7A and 7B represent a bottom view of one component of a two-component device of the present invention illustrating a flip-tab two-stage release liner system. As shown in FIG. 7A, the adhesive-backed surface of anchoring member (16) is covered by a release liner (36). A semi-rigid tab (38) is attached to the release liner (36). A first edge (40) of the semi-rigid tab (38) is positioned parallel to wound edge (20) and attached to the release liner (36) at a position intermediate between the wound edge (20) and a second edge (39) of the anchoring member (16) generally opposite the wound edge (20). A second edge (42) of the semi-rigid tab (38) extends unattached beyond the Wound edge (20) of anchoring member (16). FIG. 7C shows an end view of the device illustrated in FIG. 7A which includes semi-rigid tab (38), release liner (36) protecting the adhesive-backed surface of anchoring member (16), as well as connecting member (18) protected by another release liner (41). As shown in FIG. 7C, the semi-rigid tab (38) and a portion of the attached release liner (36) are folded over, or flipped back onto the portion of the release liner (36) which is not attached to the semi-rigid tab (38), thereby exposing the adhesive-coated surface of anchoring member (16) which includes the wound edge (20). The wound edge (20) is then attached to the skin following visual alignment, and the semi-rigid tab (38) is then gripped and removed, together with the attached release liner (36). Connecting members (18) are also shown with associated release liners (41).

The invention claimed is:

1. An interlaced two-component device for closing a laceration or incision, comprising:
   a) a first component comprising a first adhesive-backed anchoring member produced from an elastic polymeric material not reinforced with an inelastic structural component thereby providing improved adhesion relative to an otherwise identical first component produced from an inelastic material while maintaining the physical relationship between wound edges in an applied device for a period of time sufficient for the laceration or incision to heal naturally;
   b) one or more first connecting members, produced from a substantially inelastic material, adhesively attached to the first adhesive-backed anchoring member and extending from one edge thereof in a first direction;
   c) a second component comprising a second adhesive-backed anchoring member produced from an elastic polymeric material not reinforced with an inelastic structural component thereby providing improved adhesion relative to an otherwise identical second component produced from an inelastic material while maintaining the physical relationship between wound edges in an applied device for the period of time sufficient for the laceration or incision to heal;
   d) one or more second connecting members, produced from a substantially inelastic material, adhesively attached to the second adhesive-backed anchoring member and extending from one edge thereof in a second direction generally opposite to the first direction wherein the one or more first connecting members and one or more second connecting members are sufficiently spaced apart to facilitate fine adjustment of the first component relative to the second component for substantially parallel alignment of the edge of the first component with the edge of the second component during closure of the wound or incision;
   e) means for attaching the one or more first connecting members directly to the second anchoring member and means for attaching the one or more second connecting members directly to the first anchoring member, the attachment of the connecting members to the anchoring members forming attached and bridging portions of the one or more connecting members, the attached portions being attached to an anchoring member, and the bridging portions spanning the over-laceration area between the first and second anchoring members.

2. The two-component device of claim 1 further comprising a pulling element attached to the one or more first connecting members, or extensions thereof, and a pulling element attached to the one or more second connecting members, or extensions thereof.

3. The two-component device of claim 2 wherein the pulling elements and anchoring members are coded to enable user distinction.

4. The two-component device of claim 3 wherein the coding comprises an observable geometric distinction between the shape of the pulling elements and the shape of the anchoring members.

5. The two-component device of claim 3 wherein the coding comprises printed indicia enabling user distinction between pulling elements and anchoring members.

6. The two-component device of claim 3 wherein the coding comprises distinguishing colors.

7. The two-component device of claim 2 wherein the pulling elements and extensions of connecting members are removable following application of the device.

8. The two-component device of claim 2 wherein the pulling element is reinforced with a pull bar.

9. The two-component device of claim 1 which is produced from a vapor-permeable material.

10. The two-component device of claim 1 wherein the means for attaching connecting members to anchoring members is adhesive, adhesive being applied to at least a portion of the lower surface of the connecting members.

11. The two-component device of claim 10 wherein the adhesive-backed surface of each anchoring member is protected by one or more release liners, and the adhesive-backed surface of each connecting member is protected by one or more release liners.

12. The two-component device of claim 11 wherein the release liners are optionally coded to indicate sequence of removal.

13. The two-component device of claim 12 wherein the adhesive-backed surfaces of the first and second anchoring members each are protected by a first and a second release liner, the first release liner protecting adhesive-backed surfaces along the edge from which the one or more connecting members extend, and the second release liner protecting the adhesive-backed surfaces along the length of the edge of the anchoring member which is generally opposite the edge from which the one or more connecting members extend.

14. The two-component device of claim 13 wherein the coding comprises printed indicia enabling user distinction between the first release liner and the second release liner.

15. The two-component device of claim 13 wherein the coding comprises distinguishing colors between the first release liner and the second release liner.

16. The two-component device of claim 1 wherein the anchoring members are provided with one or more alignment indicators.

17. The two-component device of claim 1 wherein the anchoring members are reinforced with a wound edge bar.

18. A method for closing a laceration or incision, the method comprising:
   a) Providing an interlaced two-component device for closing a laceration or incision, comprising:
      i) a first component comprising a first adhesive-backed anchoring member produced from an elastic polymeric material not reinforced with an inelastic structural component thereby providing improved adhesion relative to an otherwise identical first component produced from an inelastic material while maintaining the physical relationship between wound edges in an applied device for a period of time sufficient for the laceration or incision to heal naturally;
      ii) one or more first connecting members, produced from a substantially inelastic material, adhesively attached to the first adhesive-backed anchoring member and extending from one edge thereof in a first direction;
      iii) a second component comprising a second adhesive-backed anchoring member produced from an elastic polymeric material not reinforced with an inelastic structural component thereby providing improved adhesion relative to an otherwise identical second component produced from an inelastic material while maintaining the physical relationship between wound edges in an applied device for the period of time sufficient for the laceration or incision to heal naturally;

iv) one or more second connecting members, produced from a substantially inelastic material, adhesively attached to the second adhesive-backed anchoring member and extending from one edge thereof in a second direction generally opposite to the first direction wherein the one or more first connecting members and one or more second connecting members are sufficiently spaced apart to facilitate fine adjustment of the first component relative to the second component for substantially parallel alignment of the edge of the first component with the edge of the second component during closure of the wound or incision;

v) means for attaching the one or more first connecting members directly to the second anchoring member and means for attaching the one or more second connecting members directly to the first anchoring member, the attachment of the connecting members to the anchoring members forming attached and bridging portions of the one or more connecting members, the attached portions being attached to an anchoring member, and the bridging portions spanning the over-laceration area between the first and second anchoring members;

b) attaching the first and second components to the skin on opposite sides of the laceration or incision, the edge of the first and second components from which the one or more connecting members extend being the edge closest to the laceration or incision;

c) closing the laceration or incision by adjusting the position of the first and second anchoring members relative to each other in both an X and a Y dimension; and d) fixing the relationship between the first and second anchoring members established in step c) by attaching the one or more first connecting members to the second anchoring member, and the one or more second connecting members to the second anchoring member.

19. The method of claim 18 wherein the device further comprises a pulling element attached to the one or more first connecting members, or extensions thereof, and a pulling element attached to the one or more second connecting members, or extensions thereof.

20. The method of claim 19 wherein the pulling elements and anchoring members are coded to enable user distinction.

21. The two-component device of claim 20 wherein the coding comprises an observable geometric distinction between the shape of the pulling elements and the shape of the anchoring members.

22. The method of claim 20 wherein the coding comprises printed indicia enabling user distinction between pulling elements and anchoring members.

23. The method of claim 20 wherein the coding comprises distinguishing colors.

24. The method of claim 19 wherein the pulling elements and extensions of connecting members are removable following application of the device.

25. The method of claim 19 wherein the pulling element is reinforced with a pull bar.

26. The method of claim 18 wherein the device is produced from a vapor-permeable material.

27. The method of claim 18 wherein the means for attaching connecting members to anchoring members is adhesive, adhesive being applied to at least a portion of the lower surface of the connecting members.

28. The method of claim 27 wherein the adhesive-backed surface of each anchoring member is protected by one or more release liners, and the adhesive-backed surface of each connecting member is protected by one or more release liners.

29. The method of claim 28 wherein the release liners are optionally coded to indicate sequence of removal.

30. The method of claim 29 wherein the adhesive-backed surfaces of the first and second anchoring members each are protected by a first and a second release liner, the first release liner protecting adhesive-backed surfaces along the edge from which the one or more connecting members extend, and the second release liner protecting the adhesive-backed surfaces along the length of the edge of the anchoring member which is generally opposite the edge from which the one or more connecting members extend.

31. The method of claim 30 wherein the coding comprises printed indicia enabling user distinction between the first release liner and the second release liner.

32. The method of claim 30 wherein the coding comprises distinguishing colors between the first release liner and the second release liner.

33. The method of claim 18 wherein the anchoring members are provided with one or more alignment indicators.

34. The method of claim 18 wherein the anchoring members are reinforced with a wound edge bar.

* * * * *